US006455037B1

(12) United States Patent
Ioannou et al.

(10) Patent No.: US 6,455,037 B1
(45) Date of Patent: *Sep. 24, 2002

(54) CELLS EXPRESSING AN αGALA NUCLEIC ACID AND METHODS OF XENOTRANSPLANTATION

(75) Inventors: Yiannis Ioannou; Robert J. Desnick, both of New York, NY (US); Mauro S. Sandrin; Ian F. C. McKenzie, both of Brunswick (AU)

(73) Assignees: Mount Sinai School of Medicine of the City University of New York, New York, NY (US); The Austin Research Institute, Heidelberg (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/742,646

(22) Filed: Nov. 1, 1996

(51) Int. Cl.[7] .................. A61K 48/00; A01N 63/00; C12N 5/00; C12N 5/06
(52) U.S. Cl. ............... 424/93.21; 435/325; 435/354
(58) Field of Search ................. 424/93.1, 93.21; 435/320.1, 325, 455, 354; 800/2, DIG. 1, 13, 14, 17, 18, 21, 22, 25

(56) References Cited

U.S. PATENT DOCUMENTS 5,356,804 A 10/1994 Desnick et al.
6,166,288 A * 12/2000 Diamond et al. ............. 800/17

FOREIGN PATENT DOCUMENTS

WO    WO 94/12628   * 11/1993
WO    WO 95/34202     12/1995

OTHER PUBLICATIONS

Houdebine, Journal of Biotechnology, vol. 34, pp. 269–287, 1994.*
Mullins et al., J. Clin. Invest., vol. 98, pp. S37–S40, 1996.*
Wall, Theriogenology, vol. 45, pp. 57–68, 1996.*
Hammer et al., J. Anim. Sci., vol. 63, pp. 269–278, 1986.*
Ebert et al., Molecular Endocrinology, vol. 2, pp. 277–283, 1988.*
McKenzie et al., Transplantation Proceedings, vol. 27, No. 1, pp. 247–248, Feb. 1995.*
McKenzie et al., Journal of Immunology, vol. 161, No. 10, pp. 5116–5119, Nov. 1998.*
McKenzie et al (1998) Transplantation 66, 754–763.*
Cohney et al (1997) Transplantation 64, 495–500.*
Sharma et al (1996) Proced. Natl. Acad. Sci. 93, 7190–7195.*
Kioke et al (1996) Xenotransplantation 3, 81–86.*
Neethling et al (1994) Transplantation 57, 959–963.*
Kaufman et al (1995) Ann. Rev. Immun. 13, 339–367.*
Miyagawa et al (1989) Transplant. Proced. 21, 520–521.*
Wall et al (1991) Proced. Natl. Acad. Sci. 88, 1696–1700.*
Calhoun et al (1985) Proced. Natl. Acad. Sci. 82, 7364–7368.*
Byrne et al., 1997, "Transgenic Pigs Expressing Human CD59 and Decay–Accelerating Factor Produce an Intrinsic Barrier to Complement–Mediated Damage", Transplantation 63:149–155.
Byrne et al., 1995, "Protection of Xenogeneic Cardiac Endothelium from Human Complement by Expression of CD59 or DAF in Transgenic Mice", Transplantation 60:1149–1156.
Chen et al., 1996, "Reduction in Gal–α 1,3–Gal Epitope Expression in Transgenic Mice Expressing Human H–Transferase", Xenotransplantation 3:69–75.
Cozzi et al., 1997, "Characterization of Pigs Transgenic for Human Decay–Accelerating Factor", Transplantation 64:1383–1392.
Diamond et al., 1996, "Characterization of Transgenic Pigs Expressing Functionally Active Human CD59 on Cardiac Endothelium", Transplantation 61:1241–1249.
McCurry et al., 1995, "Transgenic Expression of Human Complement Regulatory Proteins in Mice Results in Diminished Complement Deposition During Organ Xenoperfusion", Transplantation 59:1177–1182.

(List continued on next page.)

*Primary Examiner*—Deborah Crouch
(74) *Attorney, Agent, or Firm*—Pennie & Edmonds LLP (57) ABSTRACT

The present invention relates to methods and compositions for the reduction of xenotransplantation rejection. Specifically, the present invention relates, first, to transgenic cells, tissues, organs and animals containing transgenic nucleic acid molecules that direct the expression of gene products, including, but not limited to enzymes, capable of modifying, either directly or indirectly, cell surface carbohydrate epitopes such that the carbohydrate epitopes are no longer recognized by natural human antibodies or by the human cell-mediated immune response, thereby reducing the human immune system response elicited by the presence of such carbohydrate epitopes. In a preferred embodiment, the transgenic cells, tissues, organs and animals express nucleic acid molecules encoding functional recombinant α-Galactosidase A (αGalA) enzyme which modifies the carbohydrate epitope Galα(1,3)Gal. In a more preferred embodiment, the transgenic cells, tissues, organs and animals expressing the functional recombinant αGalA are transgenic pig cells, organs, tissues and/or animals. Second, the present invention relates to methods for xenotransplantation comprising introducing the transgenic cells, tissues and/or organs into human recipients so that a lower level of hyperacute rejection (HAR) is observed in the human recipients relative to the level of HAR observed in human recipients having received non-transgenic cells, tissues and/or organs.

17 Claims, 8 Drawing Sheets

OTHER PUBLICATIONS

Sandrin et al., 1996, "Reduction of the Major Porcine Xenoantigen Galα(1,3)Gal by Expression of α(1,2)Fucosyltransferase", Xenotransplantation 3:134–140.

Sandrin et al., 1995, "Enzymatic Remodelling of the Carbohydrate Surface of a Xenogenic Cell Substantially Reduces Human Antibody Binding and Complement–Mediated Cytolysis", Nature Medicine 1:1261–1267.

Somerville et al., 1994, "Functional Expression of Human CD59 in Transgenic Mice", Transplantation 58:1430–1435.

Fodor et al., 1994, *Proc. Natl. Acad. Sci. USA* 91, 1153–1157.

Bach et al., 1995, "Barriers to Xenotransplantation", Nature Medicine 1:869–873.

Burch et al., 1993, "Ventricular Expression of Atrial Natriuretic Peptide after Orthotopic Cardiac Transplantation", Transplantation 56:433–436.

Cairns et al., 1994, "Enzymatic Removal from Various Tissues of the Galactose α 1,3–Galactose Target Antigens of Human Antispecies Antibodies", Transplantation Proc. 26:1279–1280.

Cooper et al., 1994, "Oligosaccharides and Discordant Xenotransplantation", Immunological Rev. 141:31–58.

Galili et al., 1988, "Man, Apes, and Old World Monkeys Differ from Other Mammals in the Expression of α–Galactosyl Epitopes on Nucleated Cells", J. Biol. Chem. 263:17755–17762.

Hayes and Goldstein, 1974, "An α–D–Galactosyl–binding Lectin from *Bandeiraea simplicifolia* Seeds", J. Biol. Chem. 249:1904–1914.

Ioannou et al., 1992, "Overexpression of Human α–Galactosidase A Results in Its Intracellular Aggregation, Crystallization in Lysosomes, and Selective Secretion", J. Cell Biol. 119:1137–1150.

Kint, 1970, "Fabry's Disease: Alpha–Galactosidase Deficiency", Science 167:1268–1269.

Nowak, 1994, "Xenotransplants Set to Resume", Science 266:1148–1151.

Oriol et al., 1993, "Carbohydrate Antigens of Pig Tissues Reacting with Human Natural Antibodies as Potential Targets for Hyperacute Vascular Rejection in Pig–to–Man Organ Xenotransplantation", Transplantation 56:1433–1442.

Roush, 1995, "New Ways to Avoid Organ Rejection Buoy Hopes", Science 270:234–235.

Sandrin, 1994, "Identification of Gal(α1,3)Gas as the Major Epitope for Pig–to–Human Vascularised Xenografts", Transplantation Rev. 8:134–139.

Sandrin et al., 1994, "Characterization of cDNA Clones for Porcine α(1,3)Galactosyl Transferase: The Enzyme Generating the Galα(1,3)Gal Epitope", Xenotransplantation 1:81–88.

Sandrin and McKenzie, 1994, "Galα(1,3)Gal, the Major Xenoantigen(s) Recognised in Pigs by Human Natural Antibodies", Immunological Rev. 141:169–190.

Vaughan et al., 1994, "Galα(1,3)Gal is the Major Xenoepitope Expressed on Pig Endothelial Cells Recognized by Naturally Occuring Cytotoxic Human Antibodies", Transplantation 58:879–882.

Vaughan et al., 1991, "The Isolation of cDNA Clones for CD48", Immunogenetics 33:113–117.

Chen et al., 1996, "Reduction in Gal–α1,3–Gal Epitope Expression in Transgenic Mice Expressing Human H–Transferase", Xenotransplantation 3:69–75.

Koike et al., 1996, "Introduction of α(1,2)–Fucosyltransferase and its Effect on α–Gal Epitopes in Transgenic Pig", Xenotransplantation 3:81–86.

Koike et al., 1996, "Converting α–Gal Epitope of Pig into H Antigen", Transplantation Proc. 28:553.

Sharma et al., 1996, "Reduction in the Level of Gal(α1,3)Gal in Transgenic Mice and Pigs by the Expression of an α(1,2)Fucosyltransferase", Proc. Natl. Acad. Sci. USA 93:7190–7195.

\* cited by examiner

CELLS EXPRESSING AN αGALA NUCLEIC ACID AND METHODS OF XENOTRANSPLANTATION

This work was supported in part by an NIH grant (No. DK3045).

1. INTRODUCTION

The present invention relates to methods and compositions for the reduction of xenotransplantation rejection. Specifically, the present invention relates, first, to transgenic cells, tissues, organs and animals containing transgenic nucleic acid molecules that direct the expression of gene products, including, but not limited to enzymes, capable of modifying, either directly or indirectly, cell surface carbohydrate epitopes such that the carbohydrate epitopes are no longer recognized by natural human antibodies or by the human cell-mediated immune response, thereby reducing the human immune system response elicited by the presence of such carbohydrate epitopes. In a preferred embodiment, the transgenic cells, tissues, organs and animals express nucleic acid molecules encoding functional recombinant α-Galactosidase A (αGalA) enzyme which modifies the carbohydrate epitope Galα(1,3)Gal. In a more preferred embodiment, the transgenic cells, tissues, organs and animals expressing the functional recombinant αGalA are transgenic pig cells, organs, tissues and/or animals. Second, the present invention relates to methods for xenotransplantation comprising introducing the transgenic cells, tissues and/or organs into human recipients so that a lower level of hyperacute rejection (HAR) is observed in the human recipients relative to the level of HAR observed in human recipients having received non-transgenic cells, tissues and/or organs. The invention is demonstrated by way of the Examples presented in Sections 6–11, below, which, for example, describe the expression of functional recombinant αGalA in transgenic cells and the corresponding dramatic reduction of cell surface Galα(1,3)Gal carbohydrate such expression causes (Sections 7 and 10), further demonstrate that transgenic cells expressing functional recombinant αGalA elicit a significantly reduced level of complement-mediated cytoxicity (Section 9), and still further demonstrate that transgenic α-galA dramatically reduces the level of Galα(1,3)Gal in vivo.

2. BACKGROUND OF THE INVENTION

The severe shortage of human organs available for transplantation purposes has led to a great interest in the use of animal-to-human organ transplants, termed "xenotransplants". Extensive studies now exist regarding such xenotransplantations. See, e.g., Sandrin et al. (Sandrin, M. S. et al., 1994, Transplant. Rev. 8:134), which discusses studies involving the use of pig organs for xenotransplantation to humans.

The body's first reaction to a foreign tissue, known as hyperacute rejection (HAR), is a rapid and severe one, and represents one of the largest obstacles to the success of xenotransplantation techniques. HAR is for the most part, is mediated by antibodies and complement, there being natural human antibodies, predominantly IgG and IgM subclasses, which react with numerous molecules on xenotransplant cells, particularly endothelial cells, in vascularized transplants (Cooper, D. K. C. et al., 1994, Immunol. Rev. 141:31; Sandrin, M. S. and McKenzie, I. F. C., 1994, Immunol. Rev. 141:169). It is now generally accepted that all or most of the HAR reaction is due to the presence of human antibodies directed against the carbohydrate epitope Galα(1,3)Gal. This has been shown by absorption studies, particularly with Gal$^+$ transfected cells, and by the fact that Galα(1,3)Gal carbohydrates can block the reaction in vitro and in vivo (Sandrin, M. S. et al., 1994, Xenotransplantation 1:81).

Attempts to eradicate HAR have included removal or neutralization of complement in various procedures, using Cobra venom factor or transgenic animals expressing human complement regulatory molecules (e.g. CD46, CD55 and CD59). Other approaches have included the logistically difficult removal of antibody (Oriol, R. et al., 1993, Transplantation 56:433), and attempts to alter the antigen itself. With respect to this latter approach, the gene encoding the pig α(1,3)galactosyltransferase, which is necessary for the production of the GAlα (1,3) Gal carbohydrate, has been isolated with the aim of performing gene knockout studies by homologous recombination. Unfortunately, such procedures cannot be done in the pig. See Sandrin et al. (Sandrin, M. S. et al., 1994, Transplant. Rev. 8:134) for a review of other approaches to prevent the expression of the Galα(1,3)Gal, which include the use of anti-sense constructs but these have met with variable, in general disappointing results.

Another approach which has been attempted makes use of the enzyme α-Galactosidase A which cleaves a terminal α-linked galactosyl residue (Oriol, R. et al., 1993, Transplantation 56:433). Treatment of red blood cells, lymphocytes and endothelial cells with α-Galactosidase A inhibits their reaction with human serum and Cairns et al have demonstrated a similar phenomenon in vivo. A meeting report has reported that perfusion of tissue prior to transplantation with the bacterial α-Galactosidase A enzyme delayed the onset of HAR (Cairns, T. et al., 1994, Transplant. Proc. 26:1279). These enzyme treatment approaches, however, are difficult. For example, the enzymes are expensive and perfusion with an enzyme prior to transplant would be difficult, in reality, to accomplish, particularly in a manner which would ensure total eradication of the epitope.

In summary, therefore, while xenotransplantation represents a potential solution to the severe shortage of human donor organs which currently exists, the problem of hyper-acute rejection continues to be a major obstacle to the successful use of xenotransplantation.

3. SUMMARY OF THE INVENTION

The present invention relates to methods and compositions for the reduction of xenotransplantation rejection.

Specifically, the present invention relates, first, to transgenic cells, tissues, organs and animals containing transgenic nucleic acid molecules representing functional carbohydrate epitope-modifying genes which direct the expression of gene products that, either directly or indirectly, bring about modification of cell surface carbohydrate epitopes, including, but not limited to the Galα(1,3)Gal cell surface carbohydrate epitope, in a manner which reduces the human immune system response elicited by the resulting modified epitope relative to that response elicited by the unmodified Galα(1,3)Gal epitope. Such gene products can include, but are not limited to, carbohydrate epitope-modifying enzymes capable of modifying cell surface carbohydrate epitopes such that the carbohydrate epitopes are no longer recognized by either natural human antibodies or the human cell-mediated immune system, thereby reducing the human immune system response elicited by the presence of such carbohydrate epitopes.

In a preferred embodiment of the invention, the transgenic cells, tissues, organs and animals express transgenic nucleic acid molecules encoding functional recombinant α-Galactosidase A (αGalA) enzyme which modifies the carbohydrate epitope Galα(1,3)Gal by cleaving the terminal α-linked galactose from the carbohydrate epitope prior to its transfer to the cell surface on different molecules, thus producing cells which are phenotypically Galα(1,3)Gal minus. In a more preferred embodiment, the transgenic cells, tissues, organs and animals expressing the functional recombinant αGalA are transgenic pig cells, organs, tissues and/or animals. In yet another preferred embodiment of the invention, αGalA and H transferase genes are co-expressed in the transgenic cells, tissues, organs and animals of the invention.

Second, the present invention relates to methods for xenotransplantation comprising introducing the transgenic cells, tissues and/or organs into human recipients so that a lower level of hyperacute rejection (HAR) is observed in the human recipients relative to the level of HAR observed in human recipients having received non-transgenic cells, tissues and/or organs, thereby reducing the level of xenotransplantation rejection.

The invention is demonstrated by way of the Examples presented in Sections 6–11, below, which describe the expression of functional recombinant αGalA in transgenic cells and the corresponding dramatic reduction of cell surface Galα(1,3)Gal carbohydrate such expression causes (Sections 7 and 10), further demonstrate that transgenic cells expressing functional recombinant αGalA elicit a significantly reduced level of complement-mediated cytoxicity (Section 9), and still further demonstrate that transgenic α-galA dramatically reduces the level of Galα(1,3)Gal in vivo.

The transgenic cells, tissues, organs and animals of the invention can serve a variety of functions. For example, the transgenic cells, tissues and organs of the invention can be used as xenotransplants for introduction into human recipients. The transgenic animals of the invention can be used as sources for xenotransplant material to be introduced into human recipients or, alternatively, as sources for the production of transgenic cell lines. Alternatively, specific transgenic cells of the invention, namely bone marrow cells, may be used to produce red blood cells exhibiting an altered ABO phenotype, that is, can convert blood group B erythrocytes into erythrocytes of universal donor group O.

The term "functional carbohydrate epitope-modifying gene", as used to herein, refers to a nucleic acid sequence which encodes and directs the expression of a gene product that, either directly or indirectly, brings about modification of a cell surface carbohydrate epitope, including, but not limited to, the Galα(1,3)Gal cell surface carbohydrate epitope, in a manner which reduces the human immune system response elicited by the resulting modified epitope relative to that response elicited by the unmodified Galα(1,3)Gal epitope.

The term "functional carbohydrate epitope-modifying enzyme", as used to herein, refers to an enzyme, encoded by a functional carbohydrate epitope-modifying gene, which modifies a cell surface carbohydrate epitope, including, but not limited to the Galα(1,3)Gal cell surface carbohydrate epitope, in a manner which reduces the human immune system response elicited by the resulting modified epitope relative to that response elicited by the unmodified Galα(1,3)Gal epitope.

The term "functional αGalA" or "functional recombinant αGalA", as used to herein, refers to an αGalA enzyme which modifies the cell surface carbohydrate epitope Galα(1,3)Gal in a manner which reduces the human immune system response elicited by the resulting modified epitope relative to that response elicited by the unmodified Galα(1,3)Gal epitope.

4. BRIEF DESCRIPTION OF THE FIGURES

FIGS. 1(A–B). Hemagglutination of red blood cells following α-Galactosidase A treatment.

Direct hemagglutination assay showing the effect of pretreatment of red cells with α-Galactosidase A. IB4 lectin at 1 μg/ml, 0.5 μg/ml, 0.25 μg/ml, 125 ng/ml, 62.5 ng/ml, 31.25 ng/ml, 15.63 ng/ml, 7.81 ng/ml, 3.91 ng/ml, 1.95 ng/ml, 0.98 ng/ml was incubated with untreated red cells or cells treated with normal human serum (NHS) or with human α-Galactosidase A (HG) 600 U, 300 U or 150 U (FIG. 1A) or E.coli α-Galactosidase A (EG) 50 U, 25 U, 12.5 U or 6.25 U (FIG. 1B).

COS cells transiently co-transfected with a constant amount of α(1,3)galactosyltransferase cDNA (2.5 μg) and increasing amounts of α-Galactosidase A cDNA (horizontal axis, 0–12.5 μg). After 48 h cells were stained with IB4 lectin. Vertical axis shows intensity of cell staining with 100% staining intensity observed with cells transfected with α(1,3)galactosyltransferase alone. Transfection efficiency was 20–40%.

Cell lysates were prepared from COS cells transfected with plasmids α-Galactosidase A and α(1,3) galactosyltransferase (amounts in μg as indicated) or α-Galactosidase A alone or mock-transfected and assayed for α-Gal A activity using p-nitophenyl-α-D-galactoside as substrate.

FIGS. 4(A–B). Lysis of transfected COS cells by normal human serum.

Pooled normal human serum was tested for lysis of transfected and non-transfected COS cells in a $^{51}$Cr release lysis assay. (A) Normal human serum used at 1:5 dilution on α(1,3)galactosyltransferase-transfected cells (aGT)-transfected cells, α-Galactosidase A-transfected cells (aGdase), H transferase-transfected cells (HT), α(1,3) galactosyltransferase+H transferase-transfected cells (aGT+HT), α(1,3)galactosyltransferase+α-Galactosidase A+H transferase-transfected cells (aGT+aGdase+HT), and mock-transfected cells (mock). (B) Titer of normal human serum on mock-transfected cells and on α(1,3) galactosyltransferase-transfected cells (aGT)-transfected cells, α(1,3)galactosyltransferase+α-Galactosidase A-transfected cells (aGT+aGdase), α(1,3) galactosyltransferase+H transferase-transfected cells (aGT+HT), α(1,3)galactosyltransferase+α-Galactosidase A+H transferase-transfected cells (aGT+aGdase+HT). The vertical axis shows the percentage of dead cells and the horizontal axis dilutions of serum.

Relative fluorescence levels for control, control PIEC and PIEC cells transfected with human αGalA are shown, demonstrating the cells' relative abilities to bind natural human anti-GalA(1,3)Gal antibodies.

Bar graphs are shown depicting the relative amounts (in units/ml) of plasma αGalA enzymatic activity in transgenic mice expressing human αGalA and non-transgenic littermates.

Bar graphs are shown depicting the relative amounts (in % IB4 staining) of Galα(1,3)Gal in peripheral blood lymphocytes of transgenic mice expressing human αGalA and non-transgenic littermates, as obtained by flow cytometry measurements. Levels are expressed as a percentage of the control non-transgenic littermate IB4 staining.

5. DETAILED DESCRIPTION OF THE INVENTION

The present invention involves the design, construction and use of transgenic cells, tissues, organs and animals which express functional carbohydrate epitope-modifying genes which direct the expression of gene products, including but not limited to, enzymes, capable of modifying, either directly or indirectly, cell surface carbohydrate epitopes such that the carbohydrate epitopes are no longer recognized by either natural human antibodies or the human cell-mediated immune system, thereby reducing the human immune system response elicited by the presence of such carbohydrate epitopes, relative to the response elicited by the presence of the unmodified carbohydrate epitopes.

The following aspects of the invention are explained in the subsections below, solely for properties of description, and not by way of limitation: carbohydrate epitope-modifying gene sequences, and vectors and promoters which can be used in conjunction with such sequences for the construction of transgenes, including chimeric transgenes; methods for producing transgenic cells; methods for producing transgenic animals and establishing transgenic animal colonies by inbreeding or crossbreeding; and methods for xenotransplantation.

Further described below are Examples, presented in Sections 6–11, below, which demonstrate the invention. Specifically, the Examples describe the expression of functional recombinant αGalA in transgenic cells and the corresponding dramatic reduction of cell surface Galα(1,3)Gal carbohydrate such expression causes (Sections 7 and 10), further demonstrate that transgenic cells expressing functional recombinant αGalA elicit a significantly reduced level of complement-mediated cytoxicity (Section 9), and still further demonstrate that transgenic α-galA dramatically reduces the level of Galα(1,3)Gal in vivo.

5.1 Carbohydrate Epitope-Modifying Genes

The transgenic cells, tissues, organs and animals of the invention contain one or more functional transgenic carbohydrate epitope-modifying genes which direct the expression of functional carbohydrate epitope-modifying gene products. Such a carbohydrate epitope-modifying gene comprises a nucleic acid sequence which encodes a gene product that, either directly or indirectly, brings about modification of a cell surface carbohydrate epitope, including, but not limited to the Galα(1,3)Gal cell surface carbohydrate epitope, in a manner which reduces the human immune system response elicited by the resulting modified epitope relative to that response elicited by the unmodified carbohydrate epitope. The nucleic acid can include, but is not limited to, a cDNA sequence or a genomic sequence.

In a preferred embodiment of the invention, the carbohydrate epitope-modifying gene is an αGalA gene. In another preferred embodiment of the invention, the carbohydrate epitope-modifying gene of interest is coexpressed in the transgenic cells, tissues, organs and/or animals of the invention with a functional H transferase gene, the nucleic acid sequence of which is well known to those of skill in the art.

Carbohydrate epitope-modifying genes can include, but are not limited to genes which encode carbohydrate epitope-modifying enzymes. In a preferred embodiment of the invention, the carbohydrate epitope-modifying enzyme is a functional αGalA enzyme. In addition to αGalA, such enzymes can include, for example, functional sialidase enzymes and lactosaminidase enzymes which modify cell surface carbohydrate epitopes such that the modified epitopes elicit a reduced human immune system response relative to the unmodified epitopes.

Additionally, the carbohydrate epitope-modifying genes can include, for example, nucleic acid sequences which encode antisense oligonucleotide molecules which act to inhibit the transcription of genes whose expression is necessary for the production of the cell surface carbohydrate epitope of interest, e.g., the Galα(1,3)Gal epitope. For example, such carbohydrate epitope-modifying genes can include nucleic acid sequences which encode antisense oligonucleotides complementary to transcripts produced by genes which encode transferase enzymes such as α(Gal1,3) galactosyltransferase enzymes.

The nucleic acid sequences encoding such carbohydrate epitope-modifying genes are well known to those of skill in the art. If there exists an instance in which the nucleic acid sequence encoding the carbohydrate epitope-modifying gene product of interest is not known, such a nucleic acid sequence can readily be obtained utilizing standard techniques well known to those of skill in the art, as discussed, below, in Section 5.1.1., using αGalA nucleic acid sequences as an example.

The nucleic acid sequences encoding the carbohydrate epitope-modifying gene products can be operatively associated with regulatory elements that direct the expression of the coding sequences. As used herein, regulatory elements include but are not limited to inducible and non-inducible promoters, enhancers, operators and other elements known to those skilled in the art that drive and regulate expression of the coding sequences within the appropriate cellular and/or subcellular location. "Appropriate location," in this context, refers to a cellular and/or subcellular location of expression that results in a modification of the cell surface carbohydrate epitope of interest which results in a reduction in the human immune response elicited by the modified epitope relative to that response elicited by the unmodified epitope.

For example, nucleotide regulatory sequences used to regulate the carbohydrate epitope-modifying gene coding sequences can include the regulatory sequences endogenous to (i.e., normally associated with) the carbohydrate epitope-modifying gene of interest itself. Alternatively, chimeric carbohydrate epitope-modifying gene constructs containing the nucleotide coding sequence for a functional carbohydrate epitope-modifying gene product, regulated by a promoter or promoter/enhancer complex not endogenous to the carbohydrate epitope-modifying gene coding sequence may be engineered as the transgene to be used in the production of the transgenic cells, tissues, organs and animals of the invention. Multiple copies of the gene or chimeric gene construct may be arranged in the vector, and multiple-copies of the gene or chimeric gene construct may be stably introduced into the transgenic cells or founder animals.

In order to produce the gene or chimeric gene constructs used in the invention, recombinant DNA and cloning methods which are well known to those skilled in the art may be utilized (see Sambrook et al., 1989, Molecular Cloning, A Laboratory Manual, 2 nd Ed., Cold Spring Harbor Laboratory Press, NY). In this regard, appropriate carbohydrate epitope-modifying gene coding sequences may be generated from cDNA or genomic clones using restriction enzyme sites that are conveniently located at the relevant positions within the sequence. Alternatively, or in conjunction with the method above, site directed mutagenesis techniques involving, for example, either the use of vectors such as M13 or phagemids, which are capable of producing single stranded circular DNA molecules, in conjunction with synthetic oligonucleotides and specific strains of *Escherichia coli* (*E. coli*) (Kunkel, T. A. et al., 1987, Meth. Enzymol. 154:367–382) or the use of synthetic oligonucleotides and PCR (polymerase chain reaction) (Ho et al., 1989, Gene 77:51–59; Kamman, M. et al., 1989, Nucl. Acids Res. 17: 5404) may be utilized to generate the necessary carbohydrate epitope-modifying nucleotide coding sequences. Carbohydrate epitope-modifying nucleotide regulatory sequences can be obtained from genomic clones utilizing the same techniques. Appropriate sequences may then be isolated, cloned, and used directly to produce transgenic cell or animals. The sequences may also be used to engineer the chimeric gene constructs that utilize regulatory sequences other than those endogenous to the carbohydrate epitope-modifying gene, again using the techniques described here. These chimeric gene constructs would then also be used in the production of transgenic cells or animals.

The discussion presented, below, in Section 5.1.1, centers, for ease of description, and not by way of limitation, on a specific carbohydrate epitope modifying gene, αGalA. It is to be understood, however, that the general teaching regarding this gene can equally apply to other carbohydrate epitope-modifying genes as well.

5.1.1. αGalA Genes

Any nucleic acid molecule which directs the expression of a functional αGalA gene product can be used as a transgene in the production of the transgenic cells, tissues, organs and animals of the present invention. As discussed in Section 3, above, the term "functional αGalA" or "functional recombinant αGalA", as used to herein, refers to an αGalA enzyme which modifies the cell surface carbohydrate epitope Galα(1,3)Gal in a manner which reduces the human immune system response elicited by the resulting modified epitope relative to that elicited by the unmodified Galα(1, 3)Gal epitope.

Such αGalA genes include, but are not limited to, αGalA gene sequences from prokaryotic species, such as *E. coli*, and eukaryotic species, plant, such as coffee, as well as human and non-human animal sequences, which encode functional αGalA. The human αGalA amino acid sequence is, for example, well known. See, e.g., U.S. Pat. No. 5,356, 804, which is incorporated herein by reference in its entirety.

Homologues of the human αGalA gene sequences are known to exist in other species. In those instances whereby sequences are not well known, they may be identified and isolated, without undue experimentation, by molecular biological techniques well known in the art. For example, an isolated αGalA gene sequence may be labeled and used to screen a cDNA library constructed from mRNA obtained from a cell type known to or suspected of expressing αGalA derived from the organism of interest. Hybridization conditions will generally be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

Further, a previously unknown αGalA gene sequence may be isolated by performing PCR using two degenerate oligonucleotide primer pools designed on the basis of known αGalA amino acid sequences. The template for the reaction may be cDNA obtained by reverse transcription of mRNA prepared from cell lines or tissue known or suspected to express an αGalA gene. The PCR product may be subcloned and sequenced to ensure that the amplified sequences represent the desired αGalA sequences. The PCR fragment may then be used to isolate a full length cDNA clone by a variety of methods. For example, the amplified fragment may be used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source, i.e., one known to or suspected of expressing functional αGalA. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

It is to be understood that, due to the degeneracy of the nucleotide coding sequence, other αGalA DNA sequences, in addition to those either described above or isolated via the techniques described above, can also encode a functional αGalA gene product. Specifically, a functional αGalA gene can comprise any nucleic acid sequence which encodes the amino acid sequence of a functional αGalA gene product. For example, an αGalA nucleic acid sequence can include a nucleic acid sequence that hybridizes to the complement of the coding sequence of a known αGalA gene such as, for example, the sequence of the human αGalA gene disclosed in U.S. Pat. No. 5,356,804, under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3), and encodes a functional αGalA gene product and/or hybridizes under less stringent conditions, such as moderately stringent conditions, e.g., washing in 0.2×SSC/0.1% SDS at 42° C. (Ausubel et al., 1989, supra), yet which still encodes a functional αGalA gene product.

5.2 Production of Transgenic Animals

Animals of any species, including but not limited to mice, rats, rabbits, guinea pigs, pigs, micro-pigs, and non-human primates, e.g., baboons, squirrel monkeys and chimpanzees may be used to generate the transgenic animals of the invention, with pigs and micro-pigs being preferred.

A transgenic animal is a non-human animal containing at least one foreign gene, called a transgene, in its genetic material. In the present instance, this transgene represents a carbohydrate epitope-modifying gene. Preferably, the transgene is contained in the animal's germ line such that it can be transmitted to the animal's offspring. In such an instance, the animal is referred to as a "founder animal".

Transgenic animals may carry the transgene in their cells or in some, but not all their cells (i.e., the transgenic animals may be genetically mosaic). See, for example, techniques described by Jacobovits, 1994, Curr. Biol., 4:761–763. For xenotransplantation purposes, however, the cells, tissues or organs which are to be introduced into human recipients should contain and express the carbohydrate epitope-modifying gene of interest.

The transgene may be integrated as a single transgene or in concatamers, e.g., head-to-tail tandems or head-to-head tandems. The transgene may also be selectively introduced into and activated in a particular cell type by following, for example, the teaching of Lasko et al. (Lasko, M. et al., 1992, Proc. Natl. Acad. Sci. USA 89:6232–6236). The regulatory sequences required for such a cell-type specific activation will depend upon the particular cell type of interest, and will be apparent to those of skill in the art.

Any technique known in the art may be used to introduce the transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321; Wheeler, M. B., 1994, WO 94/26884, which is incorporated herein by reference in its entirety); electroporation of embryos (Lo, 1983, Mol Cell. Biol. 3:1803–1814); cell gum; transfection; transduction; retroviral infection; adenoviral infection; adenoviral-associated infection; liposome-mediated gene transfer; naked DNA transfer; and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety).

Once the founder animals are produced, they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene.

Among the preferred transgenic animals are transgenic ungulates, including but not limited to transgenic pigs. Methods for constructing such transgenic animals are well known to those of skill in the art. See, e.g., international application numbers WO 94/26884 and WO 95/04744, which are hereby incorporated by reference in their entirety.

5.3 Transgenic Cells, Tissues and Organs

Any transgenic cell, including but not limited to transgenic bone marrow cells, peripheral blood stem cells, liver cells, kidney cells, islet cells, etc., are to be considered within the scope of the present invention. Further, any tissue or organ, including but not limited to, liver, kidney, muscle, heart, lung, pancreas, skin thyroid, parathyroid, adrenal cortex, adrenal medulla, thymus, cartilage, bone, etc. are to be considered within the scope of the present invention.

The transgenic cells, tissues and organs of the invention may be produced by a variety of methods which are well known to those of skill in the art. For example, the transgenic cells, tissues and organs of the invention may be obtained from the transgenic animals described, above, in Section 5.2.

With respect to transgenic cells, primary cultures of cells derived from the transgenic animals of the invention may be utilized, or, preferably, continuous cell lines can be generated. Such continuous cell lines can be obtained utilizing techniques well known to those of skill in the art, such as, for example, techniques described by Small et al., 1985, Mol. Cell. Biol. 5:642–648.

In addition to obtaining cells from the transgenic animals of the invention, cells of a cell type of interest may be transfected with carbohydrate epitope-modifying sequences capable of expressing a functional carbohydrate epitope modifying gene product within the cell, thus yielding transgenic cells of the invention. Transfection of cells with transgenic nucleic acid sequences can be accomplished by utilizing standard techniques such as, for example, those techniques described, above, in Section 5.2. Additionally, see, for example, Ausubel, 1989, Current Protocols in Molecular Biology, (Green Publishing Associates and Wiley Interscience, N.Y.) Transfected cells should be evaluated for the presence of the transgenic nucleic acid sequences, for expression and accumulation of the transgenic carbohydrate epitope-modifying gene product. Further, the transgenic cells should be evaluated for an ability to exhibit modified cell surface carbohydrate epitopes of interest.

5.4 Selection and Characterization of the Transgenic Cell, Tissues, Organs and Animals The transgenic cells, tissues, organs and animals that are produced in accordance with the procedures detailed in Sections 5.2 and 5.3 should be screened and evaluated to select those cells, tissues, organs and animals which may be used as suitable xenotransplant material or xenotransplant material sources.

Initial screening may be accomplished by Southern blot analysis or PCR techniques to that integration of the transgene has taken place. The level of carbohydrate epitope-modifying gene hRNA expression in the transgenic cells, tissues, organs and animals may also be assessed using techniques which include but are not limited to Northern blot analysis of samples, in situ hybridization analysis, and reverse transcriptase-PCR (rt-PCR).

The carbohydrate epitope-modifying transgenic cells, issues, organs and/or animals that express mRNA or protein (detected immunocytochemically, using appropriate antibodies) at easily detectable levels should then be further evaluated to identify those animals which display modified cell surface carbohydrate epitopes. For example, histopathological evaluation of transgenic material can be carried out using antibodies directed against the cell surface epitope of interest, coupled with standard techniques well known to those of skill in the art.

5.5 Uses of the Transgenic Cells, Tissues, Organs and Animals

The transgenic cells, tissues, organs and animals of the invention can serve a number of functions, both in vitro and in vivo. For example, the transgenic material can serve as xenotransplantation material or as the source for xenotransplantation material. The use of the transgenic material of the invention as xenotransplantation material serves to lower level of hyperacute rejection (HAR) observed in human recipients relative to the level of HAR observed in human recipients having received non-transgenic cells, tissues and/or organs, thereby reducing the level of xenotransplantation rejection.

Alternatively, specific transgenic cells of the invention, namely bone marrow cells, may be used to produce red blood cells exhibiting an altered ABO phenotype, that is, can convert blood group B erythrocytes into erythrocytes of universal donor group O.

With respect to xenotransplantation utilizing the transgenic material of the invention, any technique for transplanting donor material into recipients can be utilized. Such techniques are well known to those of skill in the art. Transfer methods include, for example, methods of introducing cells such as those listed, above, in Section 5.3, including but not limited to blood cells and bone marrow cells, and methods for introducing tissues and organs such as those listed, above, in Section 5.3, including heart, liver, lung and kidney tissues and/or organs.

6. EXAMPLE

Reduction Of Red Cell Hemagglutination Is Reduced Following Treatment With α-Galactosidase A In the Example presented herein, it is demonstrated that αGalA brings about a reduction in red blood cell hemagglutination.

6.1 Materials and Methods

Figure 1A:
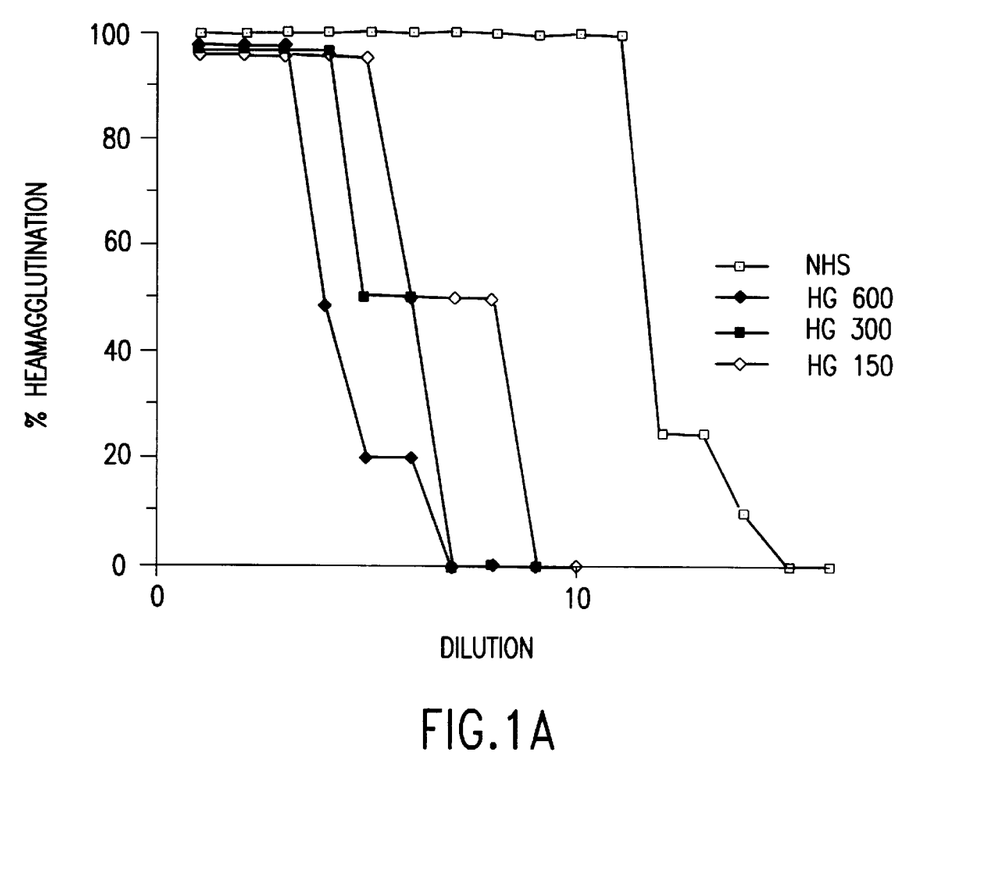
Figure 1B:
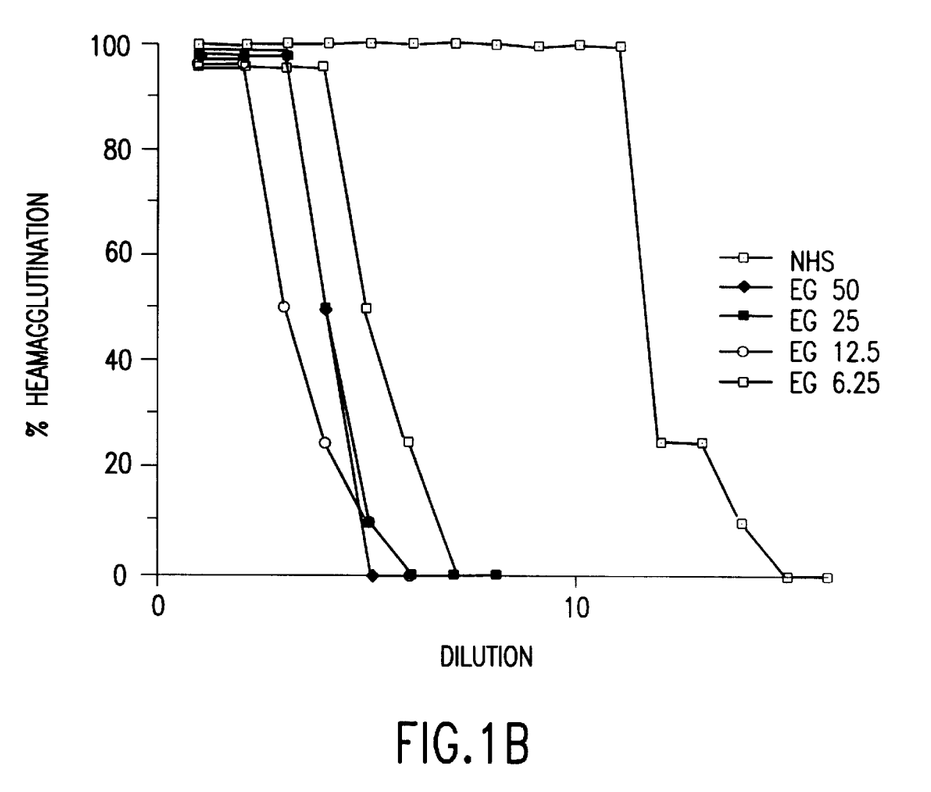

Hemagalutination Assay. Rabbit red blood cells (Galα(1, 3)Gal+) were washed in PBS and resuspended to a 2% (v/v) suspension. Cells were either untreated or were treated with human α-Galactosidase A or *E.coli*-derived α-Galactosidase A (Boehringer Mannheim, Germany) at varying concentrations (see FIG. 1 legend) for 2 h at 37° C. The cells were washed, and hemagglutination assays performed by incubating dilutions of IB4 lectin (isolated from *Griffonia simplicifolia* (Sigma, St. Louis, Mo.; Hayes, C. E. and Goldstein, I. J., 1974, J. Biol. Chem. 249:1904) in 50 μl in microtiter plates mixed with 50 μl aliquots of α-Galactosidase A-treated and untreated red blood cells and agglutination end-point titer determined after 2 h.

6.2 Results

The ability of α-Galactosidase A to cleave the terminal galactose residues from Galα(1,3)Gal was examined using rabbit red blood cells as targets. The red cell surface ceramide pentahexoside is the major Galα(1,3)Gal bearing glycolipid of rabbit red blood cells (Galil, U. et al., 1988, J. Biol. Chem. 263:17755). The concentration of the Galα(1, 3)Gal specific lectin, IB4 from *Griffonia simplicifolia* (Hayes, C. E. and Goldstein, I. J., 1974, J. Biol. Chem. 249:1904), was used as an indication of antigen density before and after α-Galactosidase A treatment. Untreated red cells were agglutinated using lectin at 0.98 ng/ml (FIG. 1a). After treatment of the red cells with either human or *E.coli* α-Galactosidase A, substantially more lectin was required to agglutinate the red cells: 7.81 ng/ml of lectin after treatment of red blood cells with 150 U of human α-Galactosidase A, 15.63 ng/ml after 300 U and 125 ng/ml after 600 U (FIG. 1a). Similar results were obtained after treatment of red cells with the bacterial α-Galactosidase A: 62.5 ng/ml required after 6.25 U, 125 ng/ml after 25 U and 250 ng/ml after treatment with 50 U (FIG. 1b). Thus treatment of red cells with α-Galactosidase A decreases the level of Galα(1,3)Gal on the cell surface up to 255-fold, and represents a feasible technique to reduce the amount of antigen on red cells.

7. EXAMPLE

Expression of α-Galactosidase A cDNA Causes Reduction of Galα(1,3)Gal

The Example presented herein demonstrates that cells transfected with an αGalA cDNA brings about a decrease in the level of cell surface Galα(1,3)Gal carbohydrate epitope, relative to non-transfected cells.

7.1 Materials and Methods cDNAs, Transfection and Serology. The plasmids used in these studies: p91-AGA, which encodes human α-Galactosidase A cDNA in mammalian expression vector p91023(B)(Ioannou, Y. A. et al., 1992, J. Cell Biol. 119:1137); phAGA, which encodes cDNA for human α-Galactosidase A cDNA in mammalian expression vector pCDNA1 (Invitrogen); pPGT-3 (called ppGT), which encodes porcine α(1,3)galactosyltransferase cDNA (Sandrin, M. S. and McKenzie, I. F. C., 1994, Immunol. Rev. 141:169) and pHuLy-m3.7 (called pCD48) encoding human CD48 (Vaughan, H. A. et al., 1991, Immunogenetics 33:113), were prepared using standard techniques (Ausubel, F. M. et al., 1994, *Current Protocols in Molecular Biology*. Wiley-Interscience, New York.). COS-7 cells were maintained in Dulbecco's modified Eagles Medium (DMEM) (Trace Biosciences Pty. Ltd., Castle Hill, NSW, Australia) and were transfected (1–20 μg DNA/10 cm dish) using the DEAE-Dextran method (Vaughan, H. A. et al., 1991, Immunogenetics 33:113) using DMEM supplemented with 10% Nu-Serum (Collaborative Research Inc., Bedford, Mass.); 48 h later cells were examined for cell surface expression. Direct fluorescence of the cell surface carbohydrate epitope Galα(1,3)Gal was performed with FITC-conjugated IB4 lectin. A monoclonal antibody (mAb) specific for CD48 (ASH1360, Austin Research Institute) and FITC-conjugated goat anti-mouse IgG were used for cell surface staining of CD48 in control transfections. The expression of human α-Galactosidase A was assessed by internal staining of formaldehyde-fixed and TritonX-100-permeabilized cells with affinity purified rabbit anti-α-Galactosidase A antibodies (Ioannou, Y. A. et al., 1992, J. Cell Biol. 119:1137) followed by FITC-conjugated goat anti-rabbit IgG. Fluorescence was detected by microscopy.

α-Galactosidase A and Protein Assays. Cells were washed twice with PBS and lysed in 1% TritonX-100/Sodium phosphate pH 7.0/150 mM NaCl/1 mM EDTA buffer containing protease inhibitors on ice for 20 min. Lysates were centrifuged for 15 min at 13000 g at 4° C., supernatants collected and assayed for α-Galactosidase A activity using p-nitrophenyl-α-D-galactoside as substrate (Kint, J. A., 1970, Science 270:1268). Protein concentrations were determined by Bradford assay using bovine serum albumin as standard (Bradford, M. M., 1976, Anal. Biochem. 72:248).

7.2 Results

Figure 2:
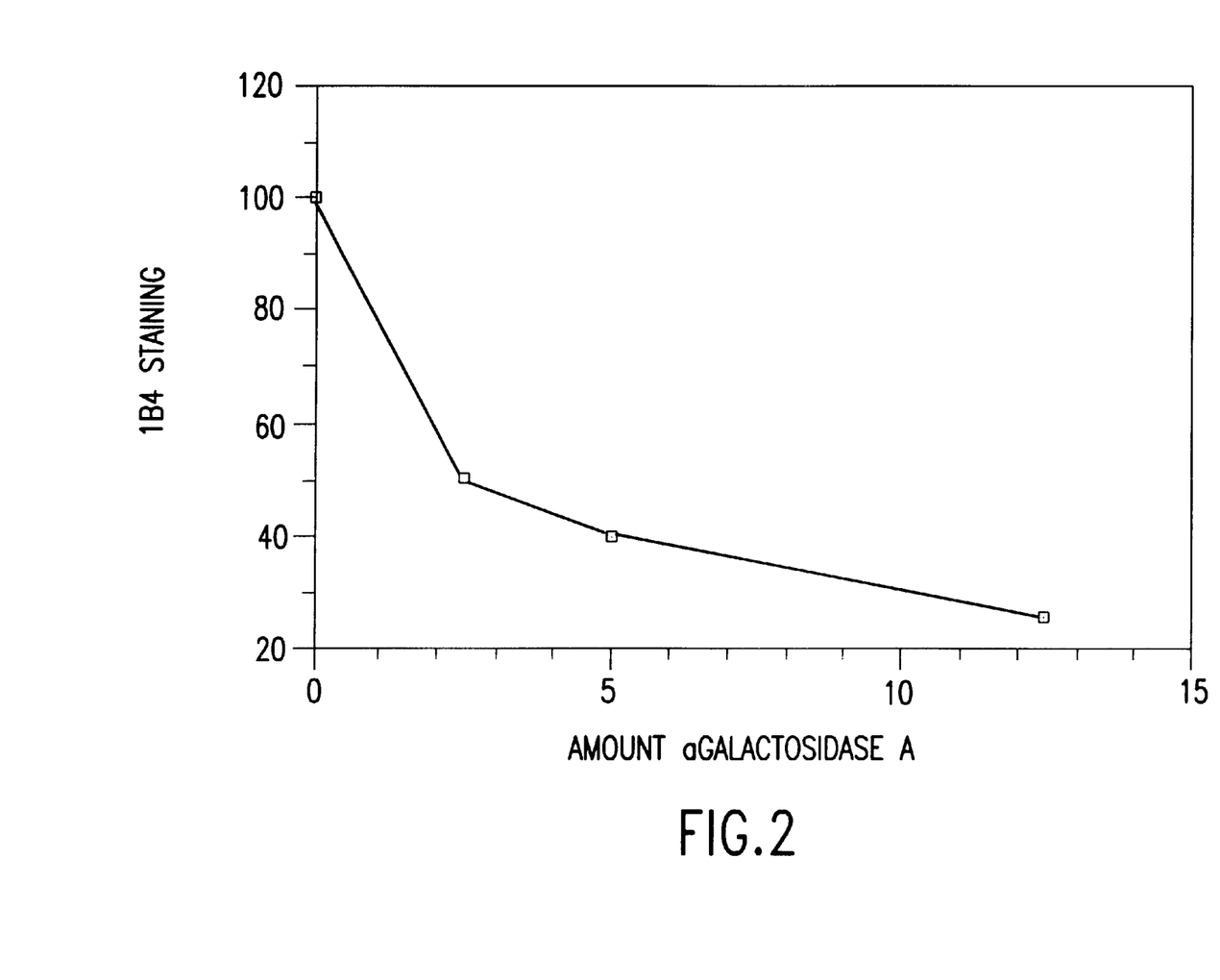
FIG. 2. Titration of α-Galactosidase A cDNA.

In order to test whether cell transfection with human α-Galactosidase A cDNA could decrease the level of Galα(1,3)Gal, α-Galactosidase A was co-expressed in COS cells expressing α-galactosyltransferase. COS cells-transfected with 2.5 μg α(1,3)galactosyltransferase cDNA alone and stained with IB4 (lectin specific for Galα(1,3)Gal) showed approximately 60% cell surface expression of Galα(1,3)Gal (FIG. 2) while cells expressing α-Galactosidase A cDNA (2.5 μg) alone showed no surface staining with IB4 (FIG. 2). Co-expression of α(1,3)galactosyltransferase cDNA+α-Galactosidase A cDNA (2.5 μg each cDNA) resulted in a significant 50% reduction of IB4 staining (FIG. 2) and a further 25% reduction in IB4 staining was seen when the amount of α-Galactosidase A cDNA co-transfected was raised to 12.5 μg, i.e., a 75% reduction. IB4 staining cells co-transfected with α(1,3)galactosyltransferase and control cDNA (human CD48) was similar to cells expressing α(1,3)galactosyltransferase alone (i.e. 60%) indicating that the observed reductions in IB4 staining with α-Galactosidase A are an accurate reflection of α-Galactosidase A altering cell surface levels of Galα(1,3)Gal and not merely a result of the co-transfection procedure.

Figure 3:
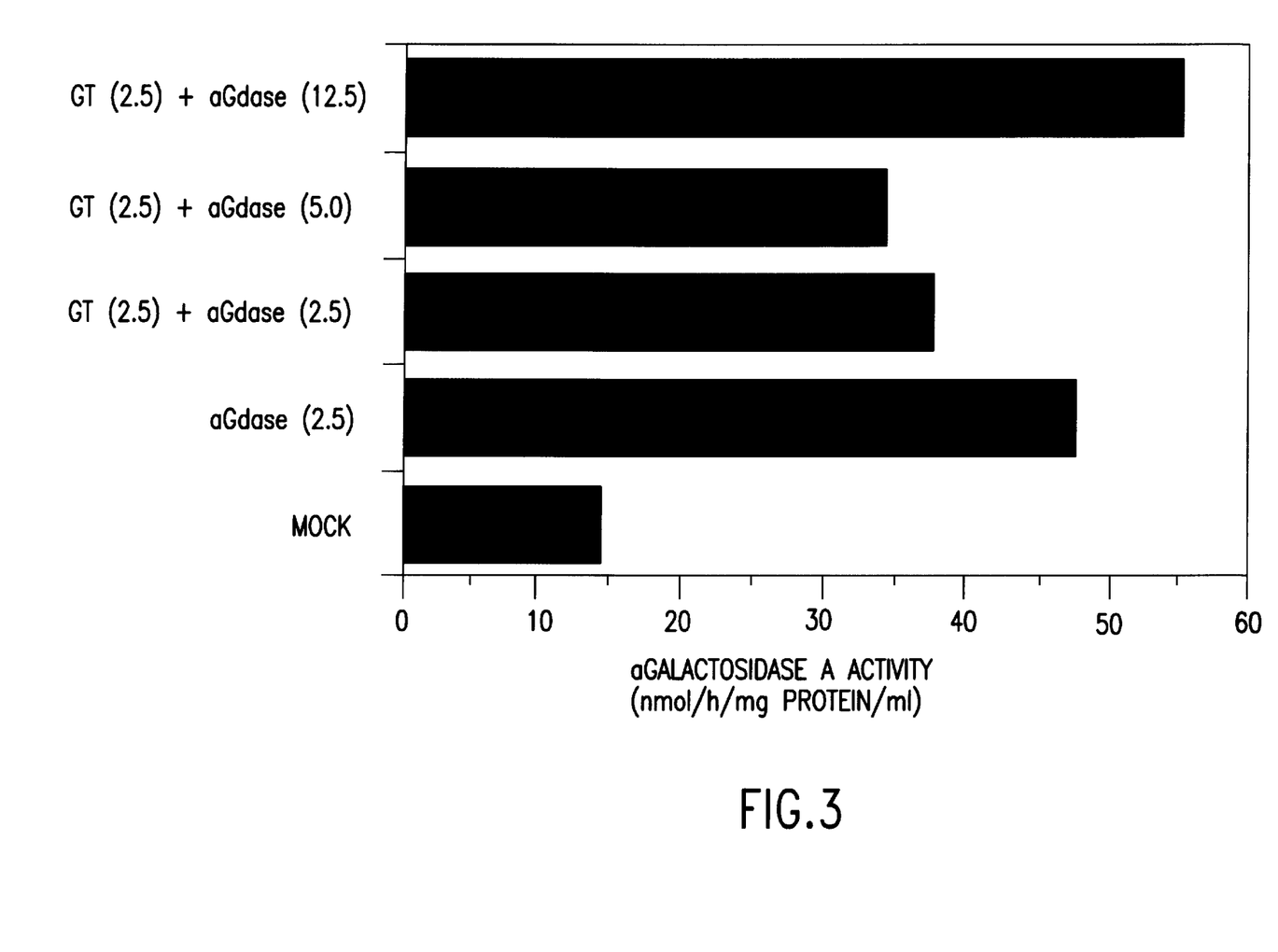
FIG. 3. α-Galactosidase A activity in transiently-transfected COS cells.

To determine the levels of α-Galactosidase A expressed in α-Galactosidase A-transfected cells, lysates were assayed using p-nitrophenyl-α-D-galactoside as a substrate for α-Galactosidase A. α-Galactosidase A activity in lysates from mock-transfected cells was 15 mmol/h/mg protein (FIG. 3). Lysates from cells transfected with α-Galactosidase A cDNA alone gave enzyme activity at 48 nmol/h/mg protein, as did lysates from cells co-transfected with α(1,3)galactosyltransferase and α-Galactosidase A (38, 35 and 56 nmol/h/mg protein for 2.5, 5 and 12.5 mg α-Galactosidase A cDNA respectively) (FIG. 3). Thus in all cases of α-Galactosidase A transfection, α-Galactosidase A activity was at least three times higher than background levels, confirming that the α-Galactosidase A was expressed and active in transiently-transfected COS cells. These findings demonstrate that expression of α-Galactosidase A after transfection of the cDNA can significantly reduce levels of Galα(1,3)Gal.

8. EXAMPLE

Co-Expression of α-Galactosidase A and H Transferase Results in a Cumulative Decrease of Galα(1,3)Gal In the Example presented herein, it is demonstrated that the co-expression of αGalA and H transferase results in a cumulative decrease in the expression of the cell surface carbohydrate epitope Galα(1,3)Gal.

8.1 Materials and Methods

The techniques utilized herein are as those described, above, in Sections 7.1.

8.2 Results

It was previously reported that a stable down-regulation of the Galα(1,3)Gal epitope in cells expressing human H transferase both in vitro and in vivo. To determine whether the effects observed with α-Galactosidase A were independent of the reduction in expression brought about by H transferase a series of co-transfection experiments were performed. COS cells were transiently co-transfected with (i) α(1,3)galactosyltransferase+H transferase cDNAs; (ii) α(1,3)galactosyltransferase+α-Galactosidase A cDNAs; or (iii) α(1,3)galactosyltransferase+H transferase+α-Galactosidase A cDNAs, and were stained on the cell surface with IB4 or UEA1 and permeabilized cells were stained for α-Galactosidase A.

In cells expressing α(1,3)galactosyltransferase cDNA+α-Galactosidase A cDNA a significant reduction in IB4 staining was observed compared with cells expressing α(1,3)galactosyltransferase cDNA alone. The reduction in IB4 staining was less than the reduction seen in cells co-transfected with α(1,3)galactosyltransferase cDNA+H transferase. Cells co-transfected with α(1,3)galactosyltransferase+H transferase+α-Galactosidase A cDNAs showed essentially no IB4 staining, i.e., staining levels approximated mock-transfected cells. Control transfections with α-Galactosidase A or H transferase cDNAs alone stained strongly with anti-α-Galactosidase A antibody or UEA1 respectively however they did not cross-react with IB-4. These results clearly demonstrate that H transferase and α-Galactosidase A have an additive effect in their ability to reduce the expression of Galα(1,3)Gal on the cell surface.

To address the question of whether a similar effect can be observed in cells constitutively expressing Galα(1,3)Gal, a human α-Galactosidase A-stable transfectant was generated using the pig endothelial cell line PIEC which is Galα(1,3)Gal$^+$. These cells have decreased levels of Galα(1,3)Gal and demonstrate that overexpression of α-Galactosidase A is a viable method of reducing this epitope.

9. EXAMPLE

α-Galactosidase A Transgenic Expression Reduces Complement-Mediated Cytotoxicity In the Example presented here, it is demonstrated that the expression of αGalA represents a viable solution to the problem of hyperacute rejection in xenotransplantation procedures, in that such expression results in a dramatic decrease in the observed level of complement-mediated cytotoxicity.

9.1 Materials and Methods

Complement lysis assay. Complement mediated lysis of α-Galactosidase A, α(1,3)galactosyltransferase and H transferase transfected COS-7 cells was performed as previously described (Vaughan, H. A. et al., 1994, Transplantation 58:879), cells were grown to confluence in 96-well plates, washed, exposed to Calcein AM (Molecular Probes Inc.) (10 μM final) for 30 min and subsequently incubated at 37° C. for 30 min in the presence of whole human serum as a source of complement. Dye released from the cells was measured using a Millipore Cytofluor 2350 fluorescence plate reader (490 nm excitation, 530 nm emission) and total cell associated dye was determined from a 1% SDS cell lysate and specific dye release calculated as a percent of total.

Other techniques. Other techniques were as described, above, in Section 7.1.

9.2 Results

Figure 4A:
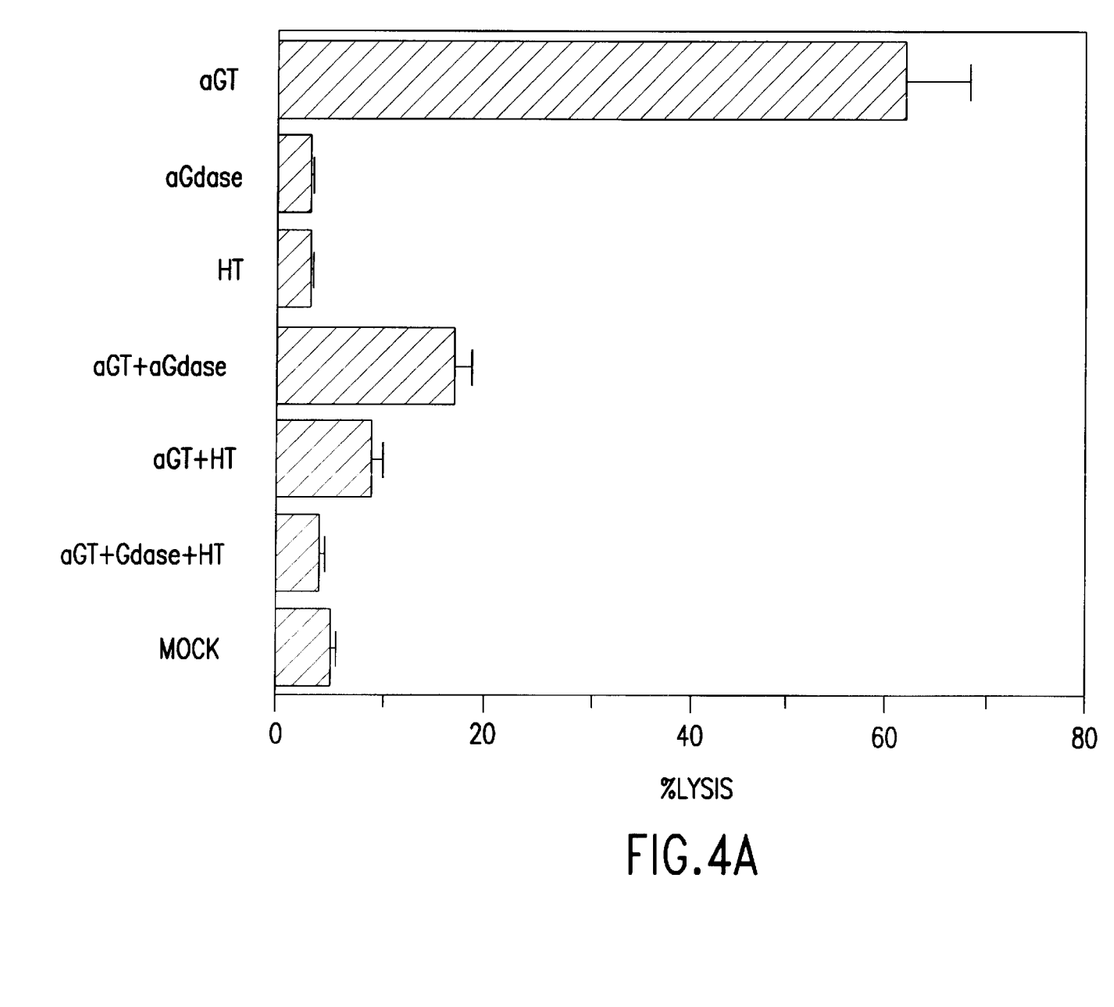
Figure 4B:
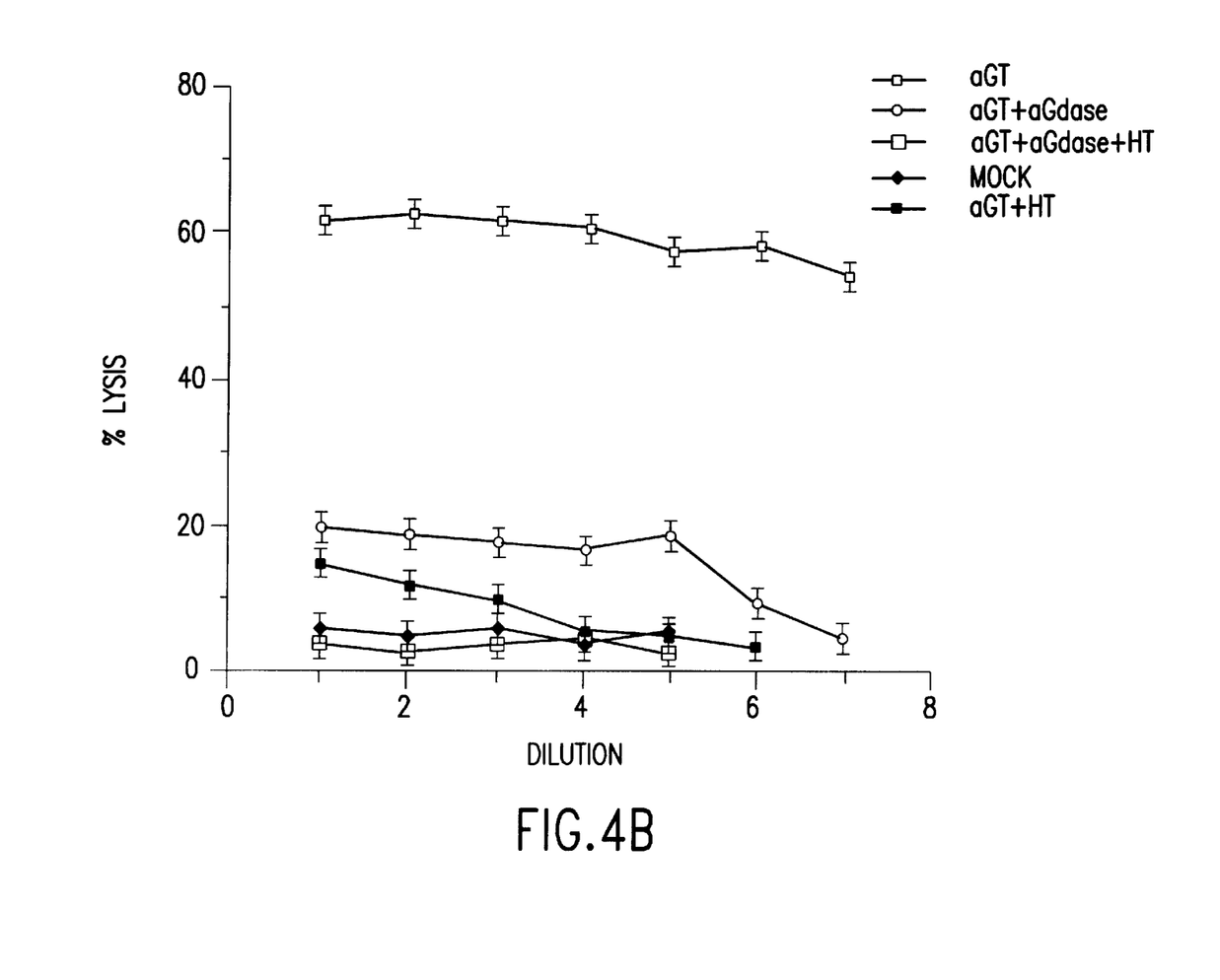

Transfection of COS cells with the pig α(1,3)galactosyltransferase cDNA clone led to the expression of Galα(1,3)Gal on the cell surface of a proportion of cells (~60%), as detected by the binding of the IB4 lectin, and these cells also became strongly reactive with natural antibodies in human serum. COS cells transfected with the α(1,3)galactosyltransferase cDNA were examined for susceptibility to lysis by human serum using a standard $^{51}$Cr release assay. The results showed that 62% specific lysis of the Galα(1,3)Gal$^+$ COS cells occurred after treatment with human serum, in contrast to a 5% background lysis of these cells (FIG. 4). Transfected COS cells were also examined for IB4 binding, which showed 65% positive cells. Thus the level of lysis was proportional to the number of cells expressing the Galα(1,3)Gal epitope. In COS cells transfected with cDNA clones encoding the α(1,3)galactosyltransferase+α-Galactosidase A 17% lysis was observed, and with the α(1,3)galactosyltransferase+H transferase 9% lysis. When COS cells were transfected with all three cDNA clones, background lysis of 4% was observed. In contrast, the human serum did not cause lysis of untransfected, α-Galactosidase A alone, H transferase alone or mock-transfected COS cells significantly above background. Specific lysis only of Galα(1,3)Gal$^+$ COS cells was observed in the presence of human serum up to a dilution of >1/256, COS cells expressing α(1,3)galactosyltransferase+α-Galactosidase A up to a dilution of 1/64, α(1,3)galactosyltransferase+H transferase up to a dilution of 1/8.

10. EXAMPLE

Transgenic αGalA Expression Reduces Galα(1,3) Gal Levels in Pig Cells

The Example presented in this Section demonstrates that the successful use of transgenic αGalA expression in pig cells to reduce the cell surface level of Galα(1,3)Gal.

10.1 Materials and Methods

The techniques utilized for the studies presented, below in Section 10.2 followed procedures as described, above, in Sections 6 through 9, and standard protocols.

10.2 Results

The results described herein further demonstrate the efficacy of using α-galactosidase in a transgenic approach to remove Galα(1,3)Gal.

Specifically, studies were conducted to test whether expression of α-galactosidase cDNA in the Galα(1,3)Gal$^+$ pig endothelial cell line PIEC would alter the cell surface expression of Galα(1,3)Gal.

Figure 5:
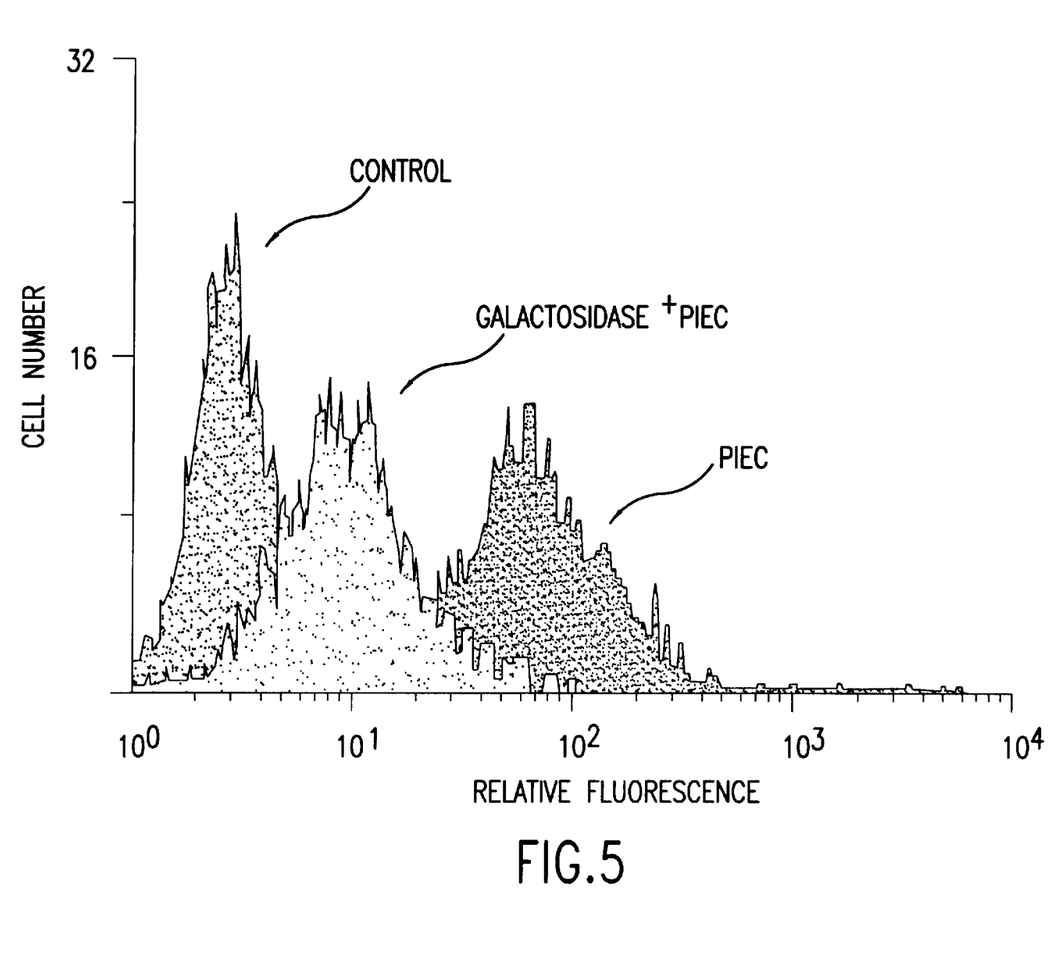
FIG. 5 flow cytometric analysis of anti-Galα(1,3)Gal antibody binding.

Stable cell lines were generated which express human α-galactosidase under a cytomegalovirus promoter. The cell lines were produced using standard calcium phosphate transfection and neomycin selection. Cells were tested for their ability to bind natural human anti-Galα(1,3)Gal antibody by standard flow cytometric analysis and demonstrated ten-fold less antibody binding than control PIEC cells demonstrating a significant reduction in cell surface Galα(1,3)Gal, as depicted in FIG. 5.

The results are consistent with the results presented in Section 7, above, which demonstrated that COS cells expressing human α-galactosidase exhibited a decreased level of Galα(1,3)Gal cell surface expression.

11. EXAMPLE

Reduction of Galα(1,3)Gal by α-galactosidase in vivo

The Example presented in this Section demonstrates the successful use of transgenic human α-galactosidase to reduce the in vivo level of Galα(1,3)Gal.

11.1 Materials and Methods

The techniques utilized for the studies presented, below in Section 11.2 followed procedures as described, above, in Sections 6 through 9, and standard protocols.

11.2 Results

Figure 6:
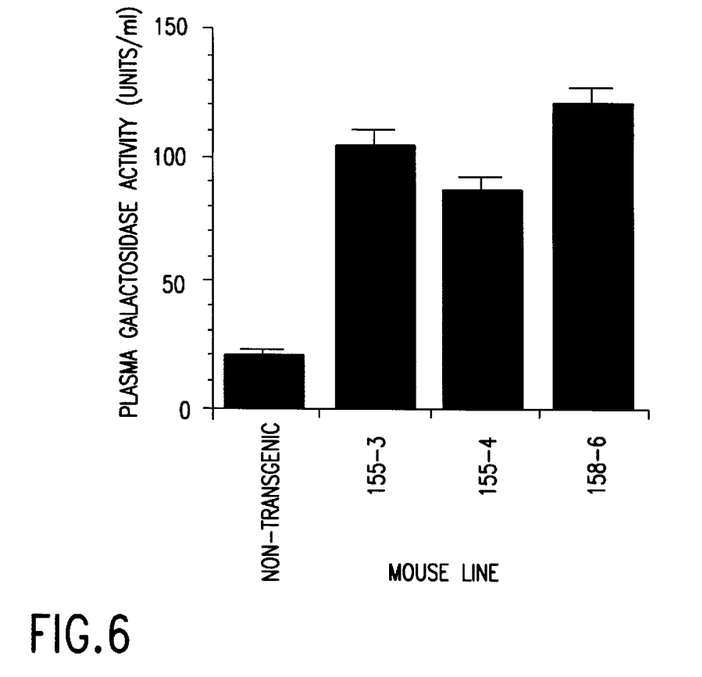
FIG. 6. α-galactosidase enzyme levels in the plasma of transgenic mice and non-transgenic littermates.

Several transgenic mouse lines expressing human α-galactosidase under an H2-K$^b$ promoter were generated using standard techniques. Results from C57BL/6 mice heterozygous for the human α-galactosidase gene demonstrated that the transgene was incorporated into the genome and was transmitted between generations. α-galactosidase enzyme levels in the plasma of transgenic mice were measured as at least four-fold higher than the level measured in non-transgenic littermates (FIG. 6).

Figure 7:
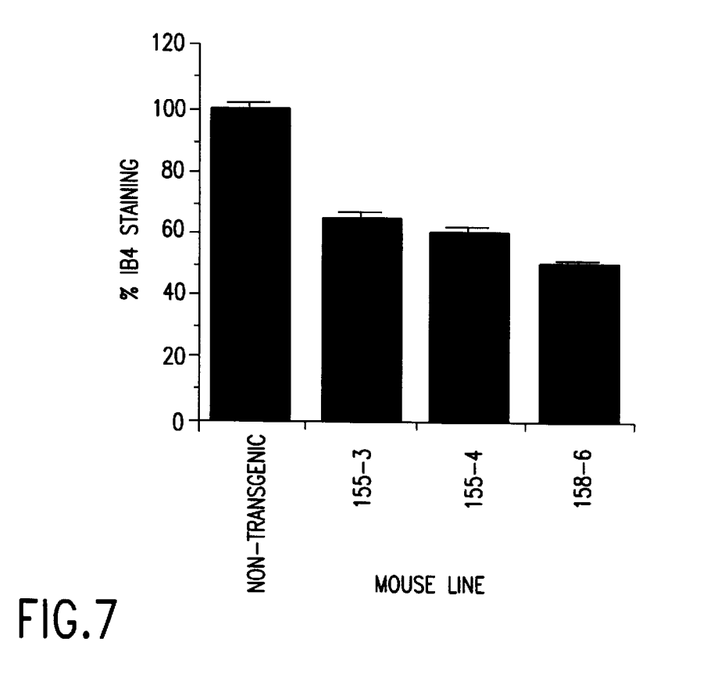
FIG. 7. Galα(1,3)Gal levels in the plasma of transgenic mice and non-transgenic littermates.

Peripheral blood lymphocytes from each transgenic line were tested for the level of Galα (1,3) Gal by staining the cell surface with IB4 (a lectin specific for Galα(1,3)Gal) and measuring by standard flow cytometry. Results are depicted in FIG. 7, with levels being expressed as a percentage of the control non-transgenic littermate IB4staining.

Transgenic mice showed between 34% and 50% reduction in their level of Galα(1,3)gal depending on the line tested, thus demonstrating the successful in vivo reduction of the epitope via the use of transgenic αGalA.

It is apparent that many modifications and variations of this invention as set forth here may be made without departing from the spirit and scope thereof. The specific embodiments described below are given by way of example only and the invention is limited only by the terms of the appended claims.

What is claimed is:

1. An isolated porcine cell that expresses:
   (a) a Galα(1,3)Gal carbohydrate epitope; and
   (b) a nucleic acid comprising an αGalA nucleic acid sequence which encodes a functional αGalA gene product and a promoter,
      wherein said cell expresses αGalA at a level that modifies the Galα(1,3)Gal carbohydrate epitope sufficiently to reduce hyperacute rejection compared to a corresponding cell which does not express αGalA.

2. The porcine cell of claim 1 further expressing an H transferase nucleic acid sequence which encodes a functional H transferase gene product.

3. An isolated porcine tissue containing the cell of claim 1 or 2.

4. An isolated porcine organ containing the cell of claim 1 or 2.

5. A method for xenotransplantation comprising: introducing the cell of claim 1 or 2 into a human recipient so that a lower level of hyperacute rejection is observed in the human recipient relative to the level of hyperacute rejection observed in a human recipient having received a cell not containing the αGalA nucleic acid sequence.

6. A method for xenotransplantation comprising: introducing the tissue of claim 3 into a human recipient so that a lower level of hyperacute rejection is observed in the human recipient relative to the level of hyperacute rejection observed in a human recipient having received a cell not containing the αGalA nucleic acid sequence.

7. A method for xenotransplantation comprising: introducing the organ of claim 4 into a human recipient so that a lower level of hyperacute rejection is observed in the human recipient relative to the level of hyperacute rejection observed in a human recipient having received a cell not containing the αGalA nucleic acid sequence.

8. A method for xenotransplantation comprising: introducing the cell of claim 1 or 2 into a recipient so that a lower level of hyperacute rejection is observed in the recipient relative to the level of hyperacute rejection observed in a recipient having received a cell not containing the αGalA nucleic acid sequence.

9. A method for xenotransplantation comprising: introducing the tissue of claim 3 into a recipient so that a lower level of hyperacute rejection is observed in the recipient relative to the level of hyperacute rejection observed in a recipient having received a cell not containing the αGalA nucleic acid sequence.

10. A method for xenotransplantation comprising: introducing the organ of claim 4 into a recipient so that a lower level of hyperacute rejection is observed in the recipient relative to the level of hyperacute rejection observed in a recipient having received a cell not containing the αGalA nucleic acid sequence.

11. An isolated murine cell that expresses:
   (a) a Galα(1,3)Gal carbohydrate epitope; and
   (b) a nucleic acid comprising an αGalA nucleic acid sequence which encodes a functional αGalA gene product and a promoter,
      wherein said cell expresses αaGalA at a level that modifies the Galα(1,3)Gal carbohydrate epitope sufficiently to reduce hyperacute rejection compared to a corresponding cell which does not express αGalA.

12. The murine cell of claim 11 further expressing an H transferase nucleic acid sequence which encodes a functional H transferase gene product.

13. An isolated murine tissue containing the cell of claim 11 or 12.

14. An isolated murine organ containing the cell of claim 11 or 12.

15. A method for xenotransplantation comprising: introducing the cell of claim 11 or 12 into a recipient so that a lower level of hyperacute rejection is observed in the recipient relative to the level of hyperacute rejection observed in a recipient having received a cell not containing the αGalA nucleic acid sequence.

16. A method for xenotransplantation comprising: introducing the tissue of claim 13 into a recipient so that a lower level of hyperacute rejection is observed in the recipient relative to the level of hyperacute rejection observed in a recipient having received a cell not containing the αGalA nucleic acid sequence.

17. A method for xenotransplantation comprising: introducing the organ of claim 14 into a recipient so that a lower level of hyperacute rejection is observed in the recipient relative to the level of hyperacute rejection observed in a recipient having received a cell not containing the αGalA nucleic acid sequence.

* * * * *